(12) United States Patent
Afzal et al.

(10) Patent No.: US 6,387,323 B1
(45) Date of Patent: May 14, 2002

(54) INTEGRATED BLOOD OXYGENATOR AND PUMP SYSTEM HAVING ACTIVE BLOOD OXYGENATOR

(75) Inventors: Thomas A. Afzal; Ronald G. Williams, both of Menlo Park, CA (US)

(73) Assignee: Cardiovention, Inc., Santa Clara, CA (US)

( * ) Notice: Subject to any disclaimer, the term of this patent is extended or adjusted under 35 U.S.C. 154(b) by 0 days.

(21) Appl. No.: 09/079,863

(22) Filed: May 15, 1998

(51) Int. Cl.[7] ............................. A61M 1/14; A61M 1/36; A61M 37/00; A61M 1/34
(52) U.S. Cl. ...................... 422/45; 422/48; 604/6.09; 604/6.11; 604/6.14
(58) Field of Search .................. 422/44–48; 604/4, 604/5, 4.01, 5.01, 6.09, 6.1, 6.11, 6.13

(56) References Cited

U.S. PATENT DOCUMENTS

| | | | |
|---|---|---|---|
| 3,466,148 A | | 9/1969 | Everett ...................... 23/258.5 |
| 3,890,969 A | * | 6/1975 | Fischel |
| 4,075,091 A | | 2/1978 | Bellhouse ...................... 210/19 |
| 4,400,275 A | | 8/1983 | Ramshaw et al. ........ 210/321.1 |
| 4,490,331 A | * | 12/1984 | Steg, Jr. ....................... 422/46 |
| 4,558,996 A | * | 12/1985 | Becker ......................... 417/374 |
| 5,162,101 A | * | 11/1992 | Cosentino et al. ............ 422/46 |
| 5,270,005 A | * | 12/1993 | Rabile ........................... 422/46 |
| 5,271,743 A | * | 12/1993 | Hattler ........................... 604/26 |
| 5,626,759 A | | 5/1997 | Krantz et al. ................ 210/645 |
| 5,626,819 A | | 5/1997 | Novello et al. ................ 422/45 |
| 5,643,794 A | * | 7/1997 | Lui et al. .................. 435/289.1 |
| 5,770,149 A | * | 6/1998 | Raible ............................ 422/46 |
| 5,830,370 A | * | 11/1998 | Maloney, Jr. et al. ........ 210/780 |
| 5,900,142 A | | 5/1999 | Maloney, Jr. et al. ........ 210/179 |

OTHER PUBLICATIONS

Berman, J. et al., "Mass Transfer to Fluids Flowing Through Rotating Nonaligned Straight Tubes," *Journal of Biomedical Engineering*, R. Skalak et al., eds., The American Society of Mechanical Engineers, 1986, pp. 342–349.

Berman, J. et al., "Oxygen Transfer to Water or Blood Flowing in a Rotating Straight Tube," Biomedical Engineering Center, Northwestern University, 4 pgs.

Berman, J. et al., "Transport in Rotating Tubular Oxygenators," Biomedical Engineering Center, Northwestern University, 4 pgs.

(List continued on next page.)

*Primary Examiner*—George R. Evanisko
*Assistant Examiner*—Patricia Bianco
(74) *Attorney, Agent, or Firm*—Fish & Neave; Nicola A. Pisano

(57) ABSTRACT

An integrated blood oxygenation and pump system suitable for use in a sterile field having a low priming volume is provided in which a blood oxygenator portion of the system includes an active element, separate from the pump, that disrupts the development of laminar flow and stagnation zones in the fiber bundle employed for gas exchange. The integrated system enables the pump and oxygenator to be used independently of one another or be rapidly reconfigured to provide both pumping action and blood oxygenation.

15 Claims, 8 Drawing Sheets

OTHER PUBLICATIONS

Gaylor, J.D.S. et al., "The Taylor–Vortex membrane oxygenator: design analysis based on a predictive correlation for oxygen transfer," *Physiological and Clinical Aspects of Oxygenator Design*, S.G. Dawids & H.C. Engell, eds., Elsevier Scientific Publishing Co., 1976, pp. 65–76.

Gaylor, J.D.S. et al., "Gas Transfer and Thrombogenesis in an Annular Membrane Oxygenator with Active Blood Mixing," *Transaction: American Society for Artifical Internal Organs, vol. XIX*, G.E. Schreiner et al., eds., Georgetown University Printing Department, 1973, pp. 516–524.

Illickal, M.M. et al., "Boundary Layer Phenomenon in Membrane Oxygenators," *Surgical Forum*, H.W. Scott et al., eds., American College of Surgeons, 1968, pp. 134–136.

Lewis, F.R. et al., "A Combined Membrane Pump–Oxygenator: Design and Testing," *Transactions: American Society for Artificial Internal Organs, vol. XX–A*, G.E. Schreiner et al., eds., Georgetown University Printing Department, 1974, pp. 253–261.

Mottaghy, K. et al., "Effect of Combined Shear, Secondary and Axial Flow of Blood on Oxygen Uptake", *Chem. Eng. Commun.: vol. 36*, Gordon and Breach Science Publishers, 1985, pp. 269–279.

Ratan, Ram S. et al., "Experimental evaluation of a rotating membrane oxygenator," *The Journal of Thoracic and Cardiovascular Surgery: vol. 53, No. 4*, B. Blades, ed., The C.V. Mosby Co., 1967, pp. 519–526.

Sakakibara, Shigeru et al., "The Centrifugal Oxygenator: Clinical Experience in 1,215 Patients," *The Annals of Thoracic Surgery: vol. 6, No. 5*, 1968, pp. 443–449.

Smeby, L.C., "The Taylor–Vortex Membrane Oxygenator," *Artificial Organs*, R.M. Kenedi et al., eds., University Park Press, 1977, pp. 70–82.

Subramanian, V.A. et al., "Comparative Evaluation of a New Disposable Rotating Membrane Oxygenator with Bubble Oxygentor," *The Annals of Thoracic Surgery: vol. 21, No. 1*, Little, Brown and Co., 1976, pp. 48–54.

* cited by examiner

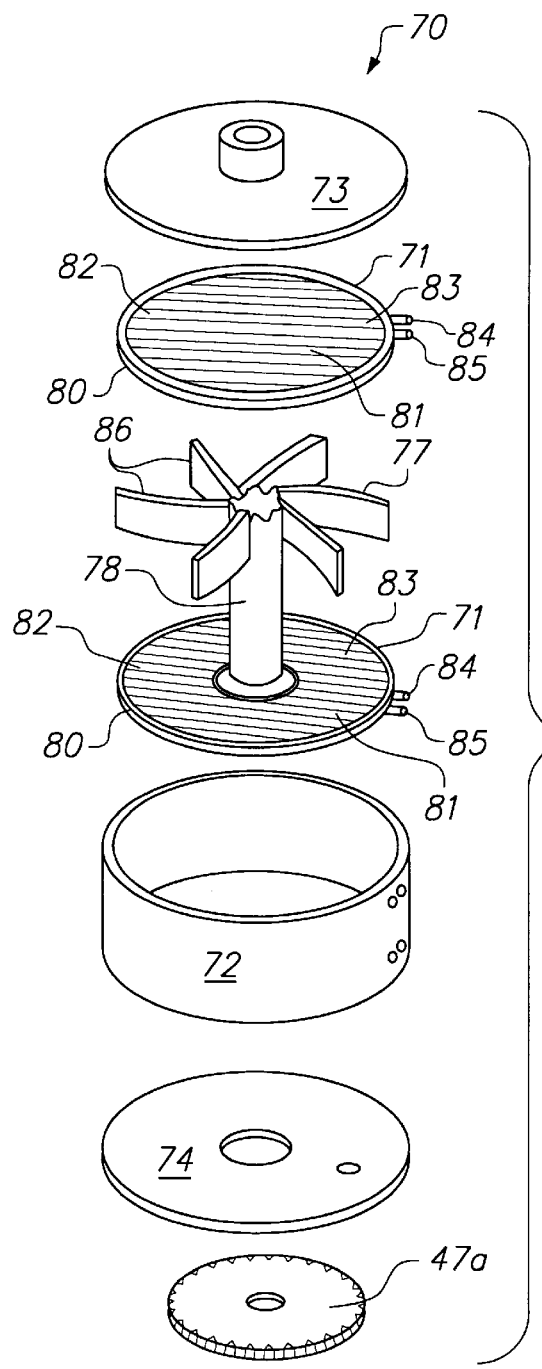
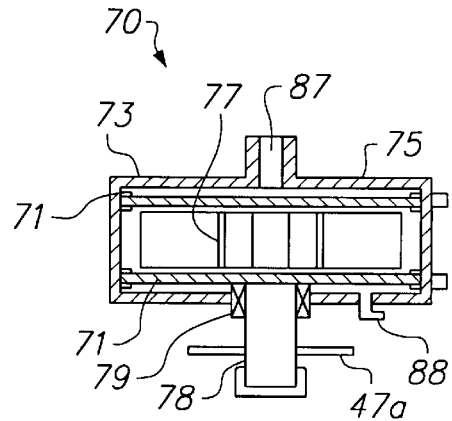
FIG. 5A
FIG. 5B

INTEGRATED BLOOD OXYGENATOR AND PUMP SYSTEM HAVING ACTIVE BLOOD OXYGENATOR

FIELD OF THE INVENTION

The present invention relates to extracorporeal systems for oxygenating and pumping blood during cardiac surgery. More specifically, the present invention relates to an integrated oxygenator and pump system wherein the oxygenator includes an active element that enhances gas diffusion, the system being sufficiently compact for use in a sterile field.

BACKGROUND OF THE INVENTION

Each year hundreds of thousands of people are afflicted with vascular diseases, such as arteriosclerosis, that result in cardiac ischemia. For more than thirty years, such disease, especially of the coronary arteries, has been treated using open surgical procedures, such as coronary artery bypass grafting. During such bypass grafting procedures, a sternotomy is performed to gain access to the pericardial sac, the patient is put on cardiopulmonary bypass, and the heart is stopped using a cardioplegia solution.

More recently, techniques are being developed, for example, by Heartport, Inc., Redwood City, Calif., that permit cardiac bypass grafting using an endoscopic approach, in which small access openings are created between the ribs and the bypass graft or heart valve repair procedure is performed guided by an image displayed on a video monitor. In the "keyhole" techniques developed by Heartport, the patient's heart is stopped and the patient is placed on cardiopulmonary bypass. Still other techniques being developed, for example, by Cardiac Thoracic Systems, Inc., of Menlo Park, Calif., enable such bypass graft procedures to be performed on a beating heart.

As a consequence of this trend towards minimally invasive cardiac surgical techniques, the need to maintain adequate space within the sterile field surrounding the small access sites has become critical. Whereas in open surgical techniques the sternotomy exposed a relatively large surgical site that the surgeon viewed directly, minimally invasive techniques require the placement of endoscopes, video monitors, and various positioning systems for the instruments that crowd the sterile field and can limit the surgeon's ability to maneuver. In recognition of the increasingly crowded environment in which a surgeon employing minimally invasive techniques must work, a need to miniaturize the equipment employed in "keyhole" cardiac surgical procedures has been recognized.

While improvements have been achieved with respect to many instruments employed in the surgical field, space-saving improvements to previously known cardiopulmonary systems have not kept pace. Such systems generally employ a series of discrete components, including a blood filter, blood reservoir, an oxygenator, a heat exchanger, a blood pump, and one or more control systems for controlling the various components. These components are typically coupled to one another in fluid communication using surgical grade tubing, and generally all of the components are maintained outside the sterile field. Such cardiopulmonary systems are generally coupled to the patient using central cannulation sites, e.g., via the vena cava or right atrium and the aorta, using lengthy tubes that extend through the sterile field and may further restrict the surgeon's ability to maneuver.

A further drawback of previously known cardiopulmonary systems is that in those systems the tubes connecting the patient to the device may constitute a relatively large volume. Consequently, such systems must be primed either with transfused blood products or saline, thus potentially compromising the patient's immune system, diluting the patient's blood, or both. In addition, such previously known systems comprise large non-native surface areas and increase the risk of further jeopardizing the patient's immune system.

In recognition of some of these disadvantages of previously known cardiopulmonary systems, attempts have been made to miniaturize and integrate some of the components of cardiopulmonary systems. U.S. Pat. No. 5,270,005 to Raible describes an extracorporeal blood oxygenation system having an integrated blood reservoir, oxygenator, heat exchanger, pump and pump motor that is controlled by cable connected to a control console. In the embodiments described in that patent, venous blood passes into a reservoir, and then through a filter, a pump, and a static array of hollow fibers for oxygen/carbon dioxide exchange before being returned to the patient. U.S. Pat. No. 5,266,265 to Raible describes a similar system.

While the foregoing patents provide integrated blood oxygenation systems having relatively compact size and reduced priming volume, those systems rely upon relatively short flow paths through the oxygenator to provide adequate oxygenation of the blood. As is well recognized in the prior art, however, oxygenators having short flow paths may provide inadequate gas exchange, due to the development of laminar flow zones adjacent to the exterior of the gas exchange elements.

Whereas laminar flow zones develop in most previously known oxygenators, the large size of the gas permeable fiber bundles used in those devices generally enable adequate mass transfer for oxygen and carbon dioxide. The compact size and static nature of the oxygenators describe in the foregoing Raible patents, however, may lead to the development of laminar flow zones and stagnation zones that impede adequate oxygen and carbon dioxide exchange. One solution to lengthen the flow path for an integrated system is described in U.S. Pat. No. 5,411,706 to Hubbard et al. The system described in that patent recirculates blood through the fiber bundle at a higher flow rate than the rate at which blood is delivered to the patient.

Apart from the recirculation technique employed in the Hubbard et al. patent, other methods are known for interrupting the development of laminar flow zones. U.S. Pat. No. 3,674,440 to Kitrilakis and U.S. Pat. No. 3,841,837 to Kitrilakis et al., which are incorporated herein by reference, describe oxygenators in which an active element stirs the blood within the oxygenator, thereby disrupting the development of laminar flow zones and enhancing mass transfer. Despite favorable test data indicating that such "active" systems do not enhance shearing damage to the blood cells, as reported, for example, in an article entitled "A Rotating Disk Oxygenator," Artificial Lungs For Acute Respiratory Failure, Academic Press, pp. 211–222 (W. Zapol ed. 1976), that technology has nevertheless been largely abandoned.

In view of the foregoing, it would be desirable to provide a compact extracorporeal blood oxygenation system that provides compact size, low priming volume, low surface area, and the ability to adequately oxygenate blood using an active element that disrupts the formation of laminar flow zones and stagnation zones with the fiber bundles of the oxygenator.

In also would be desirable to provide an integrated extracorporeal blood oxygenator and pumping system having a low priming volume and low internal surface area, thereby reducing blood contact with non-native surfaces, potential damage to blood components, and the risk of infection.

In addition, occasions arise during bypass surgery where it may be desirable to alternate between providing oxygenated blood and blood pumping. For example, in the beating-heart minimally invasive surgical methods developed by Cardio Thoracic Systems, the patient may not be placed immediately on cardiopulmonary bypass. Nevertheless, it may be desirable to use a pump to reduce the load on the heart. At a later stage of the surgery, it may be desirable to rapidly switch from a pump-assisted, beating heart method of surgery to a method involving stopping the patient's heart and placing the patient on full cardiopulmonary bypass.

It would therefore be desirable to provide an integrated extracorporeal blood oxygenator and pumping system wherein the surgeon may select pump operation either with or without inclusion of the blood oxygenator in the fluid circuit.

In addition, it is common practice to maintain a cardiopulmonary unit on standby in an operating room during use of beating heart cardiac bypass grafting procedures, and more complicated angioplasty procedures, to enable rapid conversion to open surgical techniques should complications develop during a procedure.

It further would be desirable to provide an integrated blood oxygenation and pump system having the capability to provide pump-only capacity, but which enables the patient to be placed on full cardiopulmonary support almost immediately.

It s till further would be desirable to provide an integrated extracorporeal blood oxygenator and pumping system having a low priming volume, making the system suitable for emergency back-up operation.

SUMMARY OF THE INVENTION

In view of the foregoing, it is an object of the present invention to provide a compact, integrated extracorporeal blood oxygenation and pump system that provides small size, low priming volume and the ability to adequately oxygenate blood using an active element that disrupts the formation of laminar flow zones and stagnation zones with the fiber bundles of the oxygenator.

It is another object of the present invention to provide an integrated extracorporeal blood oxygenator and pumping system having a low priming volume and low internal surface area, thereby reducing blood contact with non-native surfaces, potential damage to blood components, and the risk of infection.

It is yet another object of this invention to provide an integrated extracorporeal blood oxygenator and pump system wherein the surgeon may select pump operation either with or without inclusion of the blood oxygenator in the fluid circuit.

It is a further object of the present invention to provide an integrated blood oxygenation and pump system having the capability to provide pump-only capacity, but permits the surgeon to rapidly place a patient on full cardiopulmonary support should complications arise using a beating-heart cardiac bypass technique.

It is a still further object of the invention to provide an integrated extracorporeal blood oxygenator and pumping system having a low priming volume, making the system suitable for emergency back-up operation.

These and other objects of the invention are accomplished by providing an integrated blood oxygenation and pump system, suitable for use within a sterile field, having a low priming volume. In accordance with the principles of the present invention, the blood oxygenator includes an active element, separate from the pump, that disrupts the development of laminar flow zones and stagnation zones in the fiber bundle employed for gas exchange.

In a preferred embodiment, the integrated blood oxygenation and pump system includes a first compartment housing a pump coupled in fluid communication to a second compartment housing an active blood oxygenator. The active blood oxygenator includes an active element, separate from the pump, that enhances mixing within the blood oxygenator to reduce the development of laminar flow zones and provide adequate oxygenation of the blood, without the need for recirculation. The pump may have any one of a number of suitable configurations, and may be axial, centrifugal, roller-type or bladder-type.

In addition, the integrated system may include a valve that permits the pump to be used independently of the oxygenator, or be rapidly switched to provide both pumping action and blood oxygenation. The active oxygenator of the present invention may also be used independently of the blood pump for situations where a low flow rate is acceptable, such as in pediatric cardiac surgery.

In one embodiment, the active element comprises a rotating disk comprising hollow fibers that carry oxygen to, and carbon dioxide from, blood contacting the fibers. In alternative embodiments, the fibers are fixed within the blood oxygenator compartment, and the active element comprises an impeller that sweeps over the surfaces of the fibers to mix the blood or a movable diaphragm that agitates the blood within the oxygenator. In a yet further embodiment, the hollow fibers of the oxygenator are mounted on a disk that is agitated with an oscillatory or vibratory motion.

BRIEF DESCRIPTION OF THE DRAWINGS

Further features of the invention, its nature and various advantages will be more apparent from the accompanying drawings and the following detailed description of the preferred embodiments, in which:

FIG. 4C is a detailed view showing attachment of the gas permeable fibers in FIG. 4A;

FIGS. 5A and 5B are, respectively, an exploded perspective view and a cross-sectional view of a second embodiment of a blood oxygenator of the present invention;

FIG. 9A is an exploded perspective view of a valve suitable for use in the integrated system of the present invention, while

DETAILED DESCRIPTION OF THE INVENTION

The present invention provides an integrated blood oxygenation and pump system suitable for use with minimally invasive cardiac surgery techniques wherein the blood oxygenator includes an active element, separate from the pump, that enhances gas diffusion. In accordance with the principles of the present invention, the integrated system may be placed in or near the sterile field, and has a low priming volume, e.g., 500 cc or less.

The blood oxygenator and pump of the present invention preferably are coupled to a control console, which may be located outside the sterile field, by a cable. The integrated system may include a valve that permits the system to be readily converted from pump-only use to combined pump and blood oxygenator use. The system may therefore be advantageously used in multi-step cardiac procedures to reduce the total time a patient is placed on full cardiopulmonary bypass, or the unit may be used as an emergency back-up system.

The integrated system may further include inlet and outlet ports that permit the oxygenator to be used in a stand alone mode for pediatric applications. The system of the present invention overcomes many of the disadvantages of previously known cardiopulmonary systems, and provides the surgeon with flexibility to meet the demands of minimally invasive cardiac surgery techniques.

Figure 1:
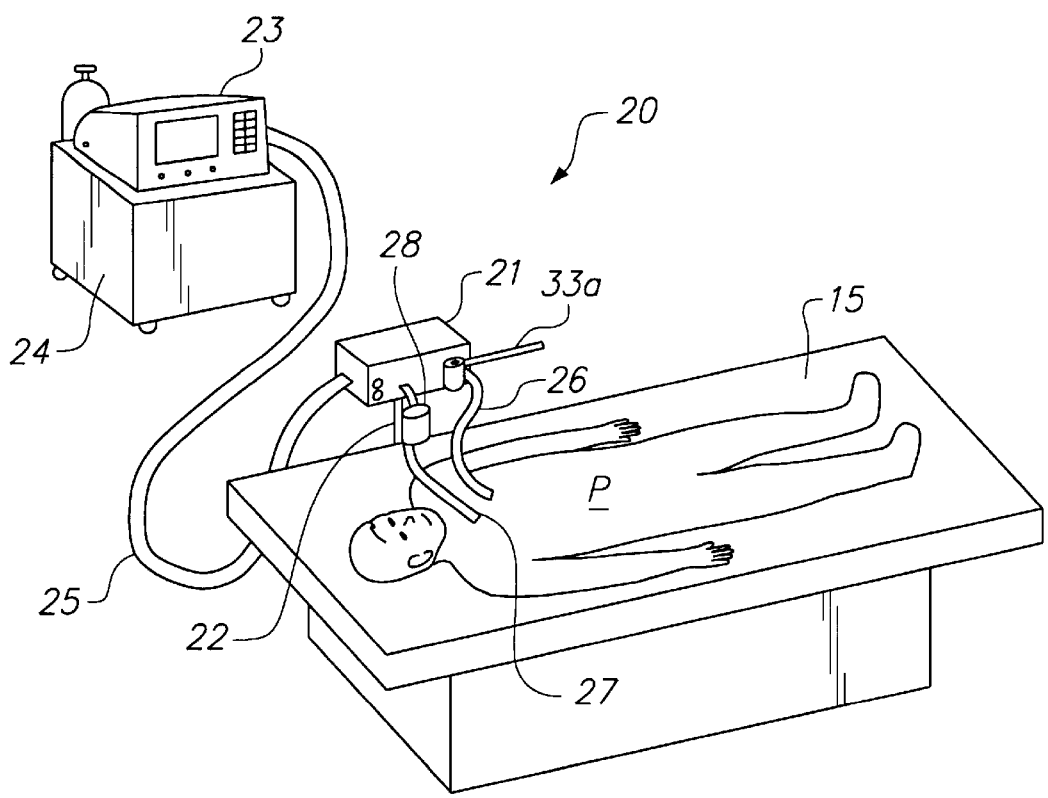
FIG. 1 is a perspective view of an illustrative integrated blood oxygenator and pump system constructed in accordance present invention in use in during cardiac surgery.

Referring now to FIG. 1, an illustrative integrated blood oxygenation and pump system constructed in accordance with the principles of the present invention is described. System 20 includes a oxygenator and pump unit 21 mounted on stand or pole 22, and which is sufficiently compact to be positioned adjacent to operating table 15 supporting patient P without limiting the surgeon's ability to maneuver within the sterile field. While unit 21 is shown disposed near an edge of table 15 for illustration purposes, it is to be understood that unit 21 preferably is located in the sterile field, near the patient's head. Oxygenator and pump unit 21 is coupled to control console 23 disposed on cart 24 via cable 25, and controls operation of unit 21 in accordance with user-selected values input at control console 23, as described hereinbelow.

Cable 25, which is preferably a flat ribbon-type cable, includes multiple lumens through which:
(1) oxygen is communicated to, and carbon dioxide is withdrawn from, the blood oxygenator of unit 21; (2) electrical or mechanical power is transmitted to unit 21 to power the pump and active element of the oxygenator; and (3) electrical leads couple blood gas parameter, temperature, flow and pressure sensors in unit 21 to control console 23. Outlet line 26 leads from a venous cannulation site to the inlet of unit 21, while return line 27 leads from the outlet of unit 21 to an arterial cannulation site. Heat exchanger 28, which may be constructed in accordance with known techniques, may be coupled in return line 27 to warm or cool the blood returned to the patient from unit 21.

Figure 2:
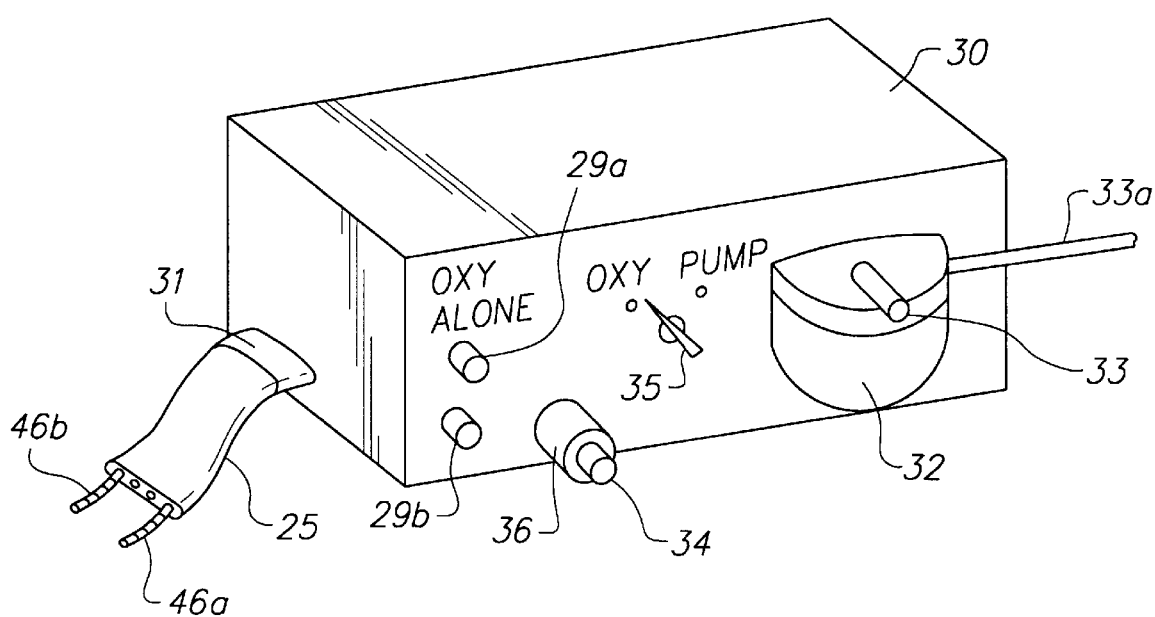
FIG. 2 is a perspective view of the integrated system of FIG. 1.

With respect to FIG. 2, unit 21 includes housing 30 having connector 31 for accepting cable 25. Blood reservoir 32 has inlet port 33 coupling unit 21 in fluid communication with outlet tubing 26, outlet port 34 coupled in fluid communication with return line 27, and selector knob 35 which is set to select either the pump alone or pump and blood oxygenator. Blood reservoir 32 may include either a hard shell, formed, for example, from polycarbonate, or a soft polyethylene bag, and preferably holds 250 ml or less of fluid.

Vacuum-assist line 33a preferably is coupled to a source of suction (not shown), and enhances flow of venous blood through outlet line and into reservoir 32 of unit 21. Alternatively, unit 21 may be mounted on stand or pole 22 at a height below the surface of table 15, to enhance drainage of venous blood to reservoir 32. Outlet port 34 preferably includes arterial filter 36 that serves as a bubble trap, and comprises a 20 or 40 micron filter medium enclosed within a polycarbonate housing.

As described hereinbelow, because the active element of the blood oxygenator may be sufficient to induce a small positive flow, e.g., on the order of 2.0 liter/min or less, separate oxygenator inlet and outlet ports 29a and 29b may be provided to permit operation of the blood oxygenator portion of unit 21 in stand-alone mode, such as in pediatric applications. These ports may include plugs that are left intact if the pump portion of the unit is to be used, or the plugs may be removed to provide oxygenator-only operation of the system.

Figure 3A:
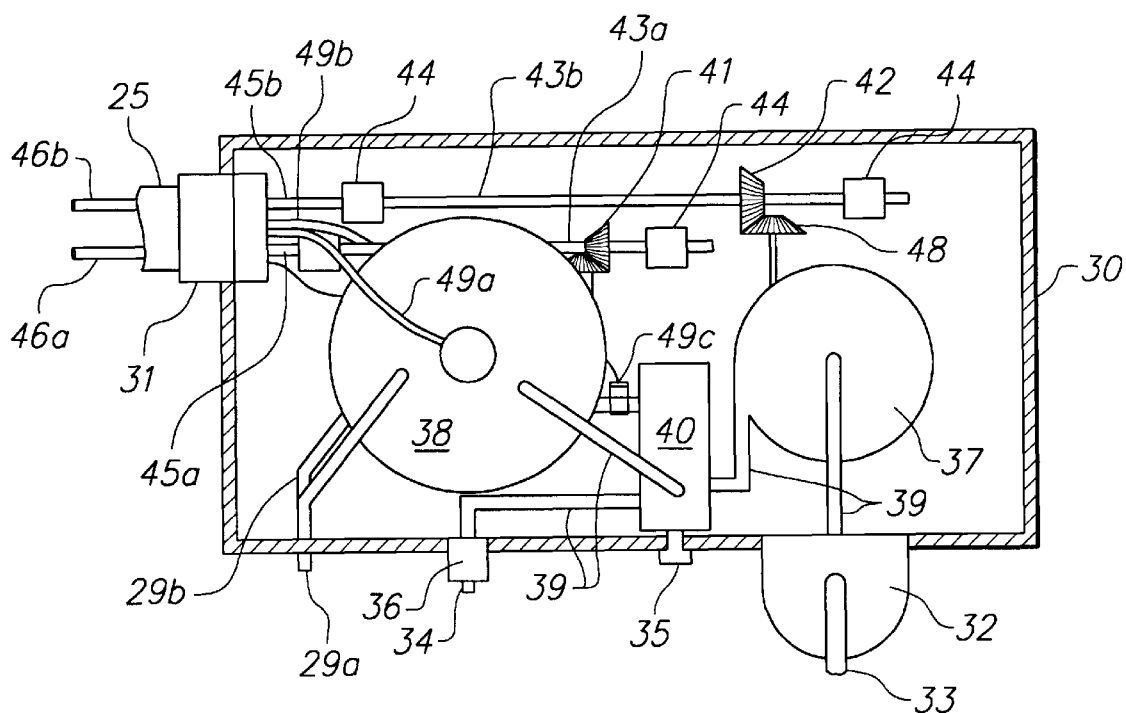
FIGS. 3A and 3B are, respectively, plan and front sectional views of the system of FIG. 1.
Figure 3B:
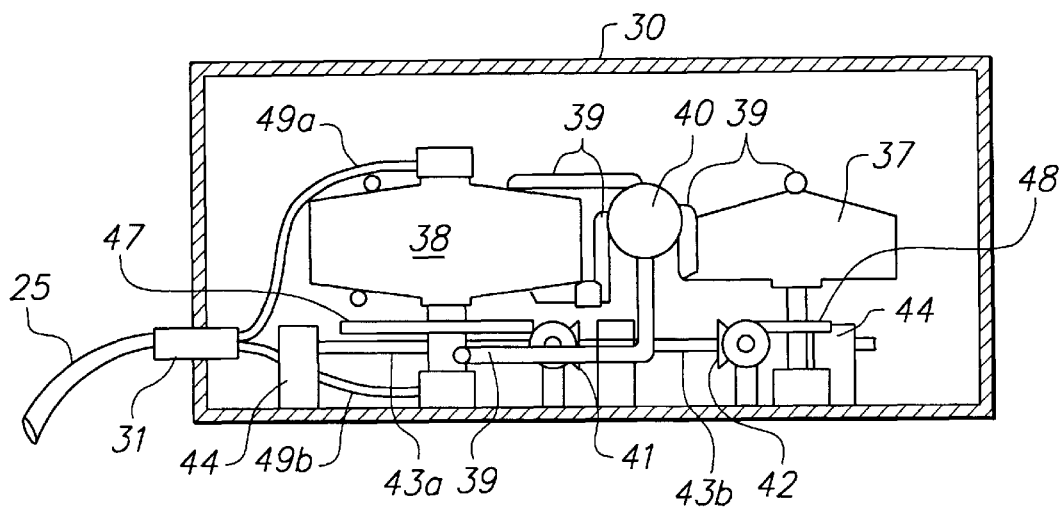

Referring now to FIGS. 3A and 3B, housing 30 contains pump 37 and blood oxygenator 38 coupled to biocompatible tubing 39 and valve 40. Tubing 39 may comprise polyvinyl chloride tubing or pipe, while valve 40 preferably is molded, machined or cast from polycarbonate or other plastic. Pump 37 has its inlet coupled to blood reservoir 32, and its outlet coupled to valve 40. Pump 37 generally should be capable of providing a maximum outlet flow rate in a range of 7 to 8 liter/min. Blood oxygenator 38 has its inlet and outlet coupled to valve 40. Depending upon the position of selector knob 35, valve 40 couples the outlet of pump 37 to outlet port 34 via arterial filter 36, or first passes the blood expelled from pump 37 through oxygenator 38, and then to outlet port 34 via arterial filter 36, as described hereinbelow.

Pump 37 and the active element of blood oxygenator 38, described in detail hereinafter, are driven by gears 41 and 42 mounted on shafts 43a and 43b, respectively. Shafts 43a and 43b are in turn mounted in housing 30 in bearings 44, and have ends 45a and 45b, respectively, configured to be coupled via connector 31 to drive cables 46a and 46b disposed in cable 25. Gears 41 and 42 preferably engage gear trains 47 and 48 coupled to the active element and pump, respectively, to drive those components at appropriate speeds. Drive cables 46a and 46b extend through cable 25 to control console 23, where they engage electric motors. Connector 31 also couples oxygen supply line 49a from control console 23 to oxygenator 38, vent line 49b from oxygenator 38 to control console 23, and various electrical leads to sensors disposed in unit 21, such as oxygen saturation sensor 49c.

Figure 4A:
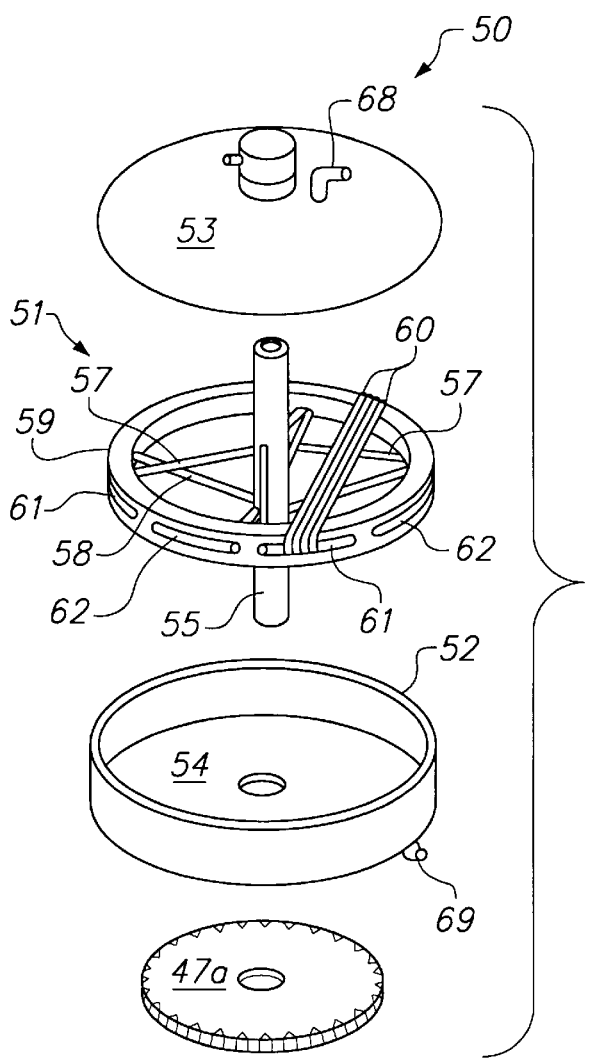
FIGS. 4A, 4B and 4C are, respectively, an exploded perspective view and a cross-sectional view of a first embodiment of a blood oxygenator constructed in accordance with the principles of the present invention.
Figure 4C:
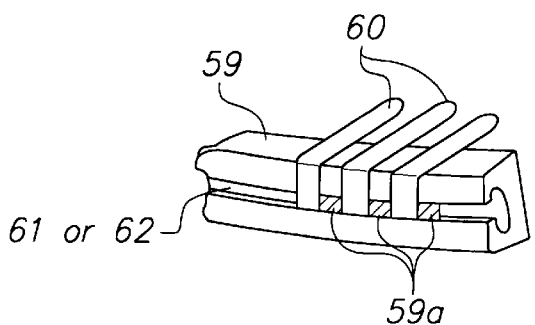
Figure 4B:
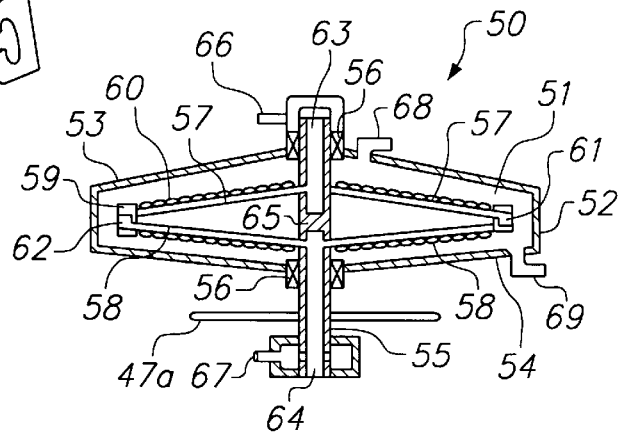

Referring now to FIGS. 4A to 4C, oxygenator 50 constructed in accordance with the present invention is described. Oxygenator 50, which may be 10–20 cm in diameter, includes oxygenator assembly 51 disposed with a compartment comprising cylindrical sidewall 52, upper plate 53 and lower plate 54. Components 52–54 are assembled using conventional techniques, such as with a suitable biocompatible adhesive.

Oxygenator assembly 51 comprises shaft 55 coupled to pluralities of hollow spokes 57 and 58, support ring 59, and multiplicity of hollow gas-permeable fibers 60 disposed chord-like across the entire area of ring 59 (for clarity, only a few of fibers 60 are shown in FIG. 4A). Shaft 55 is disposed in fluid-tight bearings 56, so that the upper and lower ends of shaft 55 extend through upper and lower plates 53 and 54, respectively. Gear 47a is affixed to shaft 55, and rotates shaft 55 at a speed proportional to rotation of shaft 43a.

The ends of fibers 60 are affixed in segmented passages 61 and 62 formed in the edge of ring 59. Passages 61 and 62 may be formed, for example, as segmented grooves in the exterior lateral face of ring 62, and then sealed by potting material 59a that fastens the ends of the multiplicity of hollow fibers 60 in position. Alternatively, a knitted hollow fiber mat may be used in place of hollow fibers 60, or a gas-permeable plate membrane material, such as described in the above-incorporated Kitrilakis patents, may be employed. One or more oxygenator assemblies 51 may be employed in oxygenator 50.

As best shown in FIG. 4B, shaft 55 includes lumens 63 and 64 that extend inwards from the upper and lower ends of the shaft and terminate at plug 65. Spokes 57 are disposed in communication with lumen 63 of shaft 55, and carry oxygen to the inlets of hollow fibers 60 via passage segments 61 in ring 59. Spokes 58 are disposed in communication with lumen 64 of shaft 55, and carry carbon dioxide from hollow fibers 60 to lumen 64 via passage segments 62 in ring 59. Accordingly, oxygen flows into lumen 63 via inlet port 66 and passes through spokes 57 to passage segments 61. Passage segments in turn serve as manifolds that distribute the oxygen to hollow fibers 60.

As oxygen diffuses through hollow fibers 60, carbon dioxide released by the blood passes into the hollow fibers, and together with the depleted oxygen stream, passes to passage segments 62. The gases collected in passage segments 62 are then drawn through spokes 58 and lumen 64, and passes through outlet port 67. These gases then pass to control console 23 via cable 25, and are exhausted to the atmosphere.

In operation, venous blood enters oxygenator 50 via inlet port 68, or tubing connected to inlet port 29a, if provided. In accordance with the principles of the present invention, oxygenator assembly 51 forms an active element that is rotated by gear 47a to enhance diffusion of oxygen into, and carbon dioxide from, blood contained in oxygenator 50. As oxygenator assembly 51 is rotated, e.g., at speeds in a range of 50 to 5000 RPM, a relatively turbulent flow is maintained outside hollow fibers 60, thereby disrupting the establishment of laminar flow zones and stagnation zones. Oxygenated blood exits from oxygenator 50 via outlet port 69 (or tubing connected to outlet port 29b, if provided). From outlet port 69, the oxygenated blood passes to valve 40, then through arterial filter 36 and outlet port 34 to return line 27.

Referring now to FIGS. 5A and 5B, an alternative embodiment of an oxygenator constructed in accordance with the principles of the present invention is described. Oxygenator 70, which may be 10–20 cm in diameter, includes oxygenator assemblies 71 disposed within a compartment comprising cylindrical sidewall 72, upper plate 73 and lower plate 74. Components 72–74 are assembled using conventional techniques, such as with a suitable biocompatible adhesive.

Oxygenator assemblies 71 are disposed within compartment 75 in spaced relation to impeller 77 mounted on shaft 78. Impeller 77 is disposed in fluid-tight bearing 79, so that lower end of shaft 78 extends through lower plate 74. Gear 47a is affixed to shaft 78, and rotates impeller 77 at a speed proportional to rotation of shaft 43a. As shown in FIG. 5B, each of oxygenator assemblies 71 comprises support ring 80 having a multiplicity of hollow fibers 81 with their ends affixed in passages 82 and 83. Passages 82 and 83 are nearly semi-circular, and serve as manifolds for carrying oxygen to, and carrying carbon dioxide away from, hollow fibers 81'. Oxygen is introduced into passage 82 via inlet port 84, and carbon dioxide and the depleted oxygen stream are exhausted through outlet port 85.

In the illustrative embodiment of FIGS. 5A and 5B, two oxygenator assemblies 71 are shown. One of skill in the art of oxygenator design will recognize that fewer or more oxygenator assemblies 71 may be employed, depending, e.g., upon the diameter of the oxygenator. In addition, a knitted hollow fiber mat may be used in place of hollow fibers 81, or a gas-permeable plate membrane material, such as described in the above-incorporated Kitrilakis patents, may be substituted for oxygenator assemblies 71.

Impeller 77 includes a plurality of straight or curved vanes 86, and is mounted in compartment 75 so that it sweeps over the surfaces of oxygenator assemblies 71 without touching the hollow fibers. Vanes 86 of impeller 77 direct blood in compartment 75 to flow over and between hollow fibers 81, thereby enhancing mixing and gas diffusion. Impeller 77 also may serve a pumping function, by reducing the pressure drop experienced by the blood as it passes through oxygenator 70. By reducing the pressure drop created by oxygenator 38, impeller 77 may obviate the need for pump 37 to be a high performance-type pump capable of outputting a high pressure head. Accordingly, by using the active element of the oxygenator to provide some pumping action in tandem with pump 37, a less expensive, lower-performance pump may be employed.

In addition, impeller 77 may be sufficient to create a positive low flow through oxygenator 70 when used in a stand-alone mode of operation without pump 37. It is expected, for example, that impeller could provide an output flow rate of up to 2.0 liter/min, thus making the oxygenator portion of unit 21 suitable for use, in stand-alone operation, in pediatric. applications. Moreover, the ability of oxygenator 70 to provide a low flow rate without the use of a separate pump permits the priming volume of the system to be in a range of 300 ml or less, thus reducing the risk of complications arising from over-dilution in pediatric applications.

In operation, venous blood enters compartment 75 via inlet port 87 and flows over oxygenator assemblies 71. Impeller 77 forms an active element that is rotated by gear 47a to enhance diffusion of oxygen into, and carbon dioxide from, blood contained in compartment 75. Impeller 77 rotates, e.g., at speeds in a range of 50 to 5000 RPM, to induce turbulent mixing within compartment 75, and to disrupt the establishment of laminar flow zones and stagnation zones within compartment 75. Oxygenated blood exits from compartment 75 via outlet port 88 and passes to valve 40, then through arterial filter 36 and outlet port 34 to return line 27.

Figure 6A:
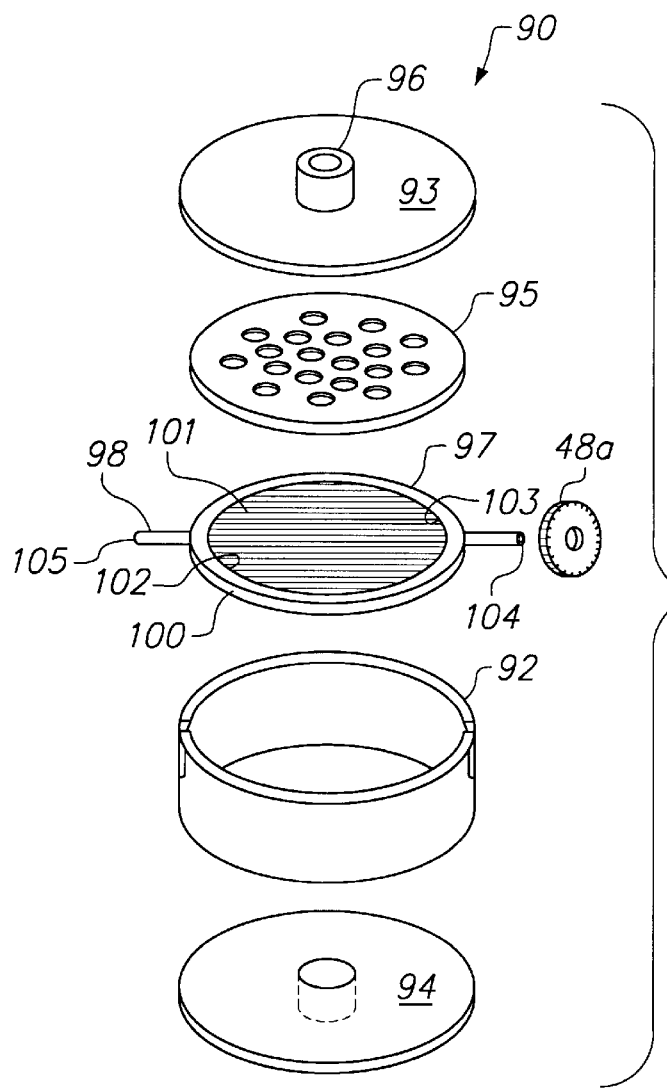
FIGS. 6A and 6B are, respectively, an exploded perspective view and a cross-sectional view of a third embodiment of a blood oxygenator of the present invention.
Figure 6B:
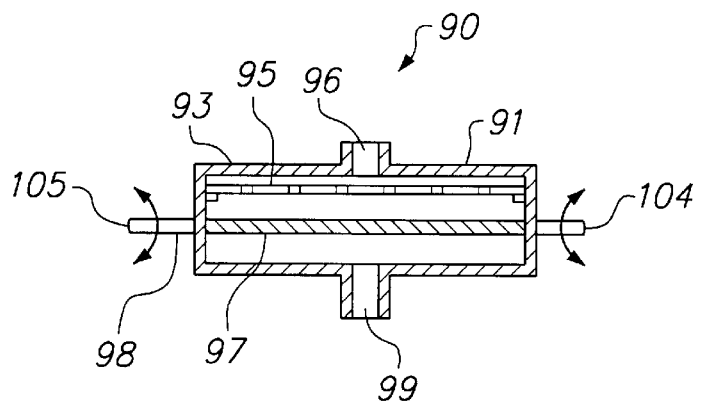

Referring now to FIGS. 6A and 6B, a yet further embodiment of the oxygenator constructed in accordance with the present invention is described. Oxygenator 90 includes baffle 95 and oxygenator assembly 97 enclosed within compartment 91 comprising cylindrical sidewall 92, upper plate 93 and lower plate assembly 94. Components 92–94 are assembled using conventional techniques, such as with a suitable biocompatible adhesive. Baffle 95, which may comprise a perforated polycarbonate sheet, is disposed in compartment 91 below inlet port 96 in upper plate 93 to distribute blood flowing into compartment 91 and enhance mixing.

Oxygenator assembly 97 is disposed within compartment 91 beneath baffle 95, and is arranged for vibratory and/or oscillatory motion on shaft 98. Shaft 98, which may be stainless steel, is mounted in fluid-tight bearings (not shown), so that the ends of shaft 98 extend through sidewall 92 of the compartment. Gear 48a is affixed to shaft 98, and imparts an angular oscillatory motion, vibrational motion, or both, to oxygenator assembly 97 at a speed proportional to rotation of shaft 43a.

Oxygenator assembly 97 comprises support ring 100 having a multiplicity of hollow fibers 101 with their ends affixed in passages 102 and 103. Passages 102 and 103 are nearly semi-circular, and serve as manifolds for carrying oxygen to, and carrying carbon dioxide away from, hollow fibers 101. Oxygen is introduced into passage 102 via inlet port 104 of shaft 98, and carbon dioxide and the depleted oxygen stream are exhausted through outlet port 105 of shaft 98. Alternatively, a knitted hollow fiber mat may be used in place of hollow fibers 101, or a gas-permeable plate membrane material, such as described in the above-incorporated Kitrilakis patents, may be substituted for oxygenator assembly 97. One or more oxygenator assemblies may be included in oxygenator 90.

In one embodiment, gear 47a is affixed to shaft 98 by gearing that first drives oxygenator assembly through several degrees in a first angular direction, and then reverses the rotation and drives the oxygenator assembly an equal distance in the reverse direction. Alternatively, a vibratory transducer may be coupled to shaft 98 to induce vibrational motion of oxygenator assembly 97, for example, by mounting a vibration-inducing motor directly in housing 30. Alternatively, the output of gear 47a may be used to drive, for example, an eccentric cam to induce vibratory motion.

In operation, venous blood enters compartment 91 via inlet port 96, passes through baffle 95, and flows over oxygenator assembly 97. Oxygenator assembly 97 and shaft 98 form an active element that is oscillated or vibrated, or both, by gear 47a to enhance diffusion of oxygen into, and carbon dioxide from, blood contained in compartment 91. Oscillation and/or vibration of oxygenator assembly 97 therefore induces turbulent mixing within compartment 91, and disrupts the establishment of laminar flow zones and stagnation zones within the compartment. Oxygenated blood exits from compartment 91 via outlet port 99 and passes to valve 40, then through arterial filter 36 and outlet port 34 to return line 27, as described hereinabove.

Figure 7A:
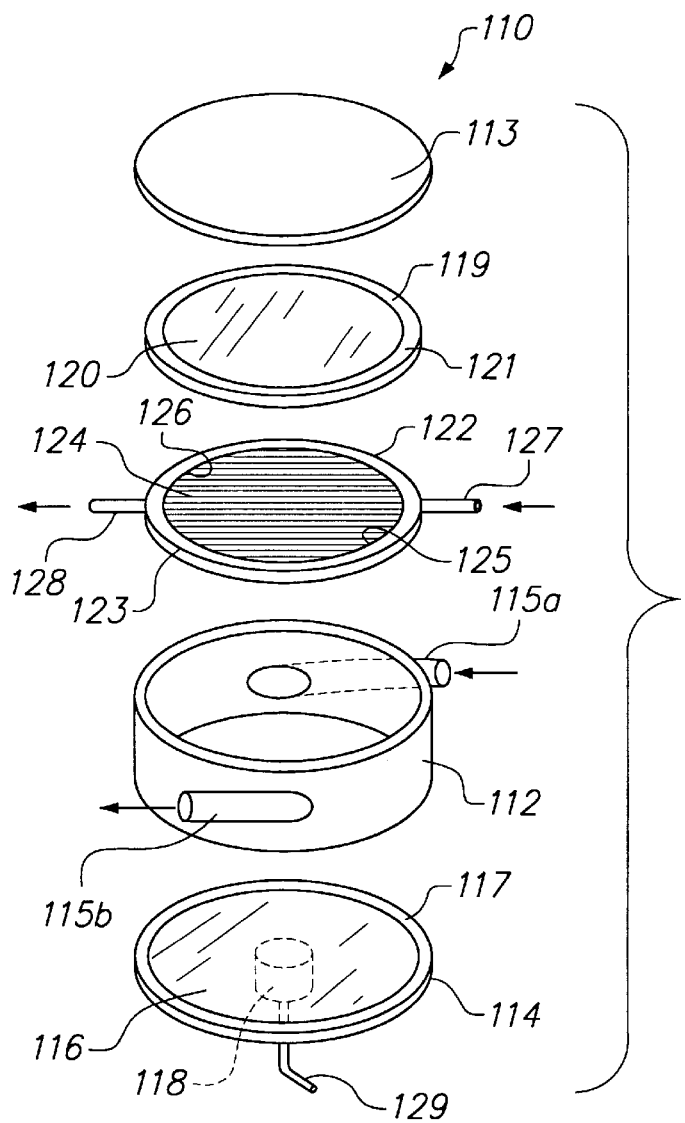
FIGS. 7A and 7B are, respectively, an exploded perspective view and a cross-sectional view of a fourth embodiment of a blood oxygenator of the present invention.
Figure 7B:
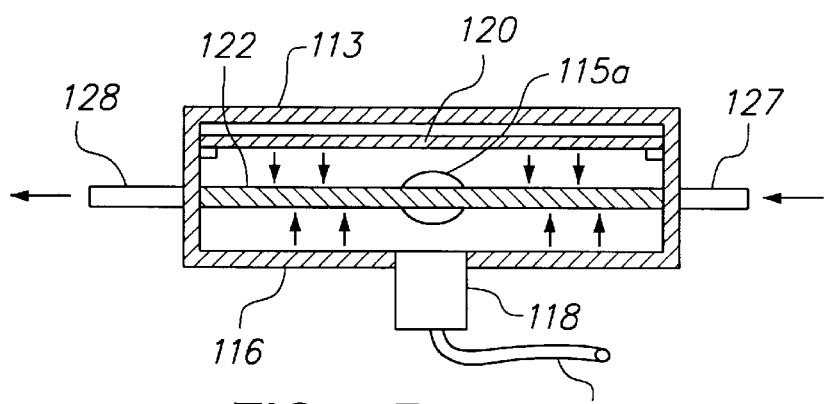

With respect to FIGS. 7A and 7B, a still further embodiment of the oxygenator constructed in accordance with the present invention is described. Oxygenator 110 includes oxygenator assembly 122 enclosed within compartment 111 defined by cylindrical sidewall 112, upper plate 113 and lower diaphragm assembly 114. Sidewall 112 includes blood inlet and outlet ports 115a and 115b, respectively. Diaphragm assembly 114 comprises elastomeric diaphragm 116, such as silicone, mounted in support ring 117, and having acoustic transducer 118 mounted in acoustic communication with diaphragm 116. Diaphragm assembly 119, also comprising elastomeric diaphragm 120 mounted in support ring 121, is mounted to sidewall 112 spaced-apart from upper plate 113.

Oxygenator assembly 122 is disposed within compartment 111 beneath between diaphragm assemblies 114 and 119, and comprises support ring 123 having a multiplicity of hollow fibers 124 with their ends affixed in passages 125 and 126. Passages 125 and 126 are nearly semi-circular, and serve as manifolds for carrying oxygen to, and carrying carbon dioxide away from, hollow fibers 124. Oxygen is introduced into passage 125 via inlet port 127, and carbon dioxide and the depleted oxygen stream are exhausted through passage 126 and outlet port 128. Alternatively, a knitted hollow fiber mat may be used in place of hollow fibers 124, or a gas-permeable plate membrane material, such as described in the above-incorporated Kitrilakis patents, may be substituted for oxygenator assembly 122. One or more oxygenator assemblies 122 may be enclosed within oxygenator 110.

Acoustic transducer 118 is coupled to control console 23 via electrical leads 129, and imparts a vibration to diaphragms 116 and 120 that agitate the column of blood enclosed within compartment 111, thereby disrupting the establishment of laminar flow or stagnation zones within oxygenator 110.

In operation, venous blood enters compartment 111 via inlet port 115a, passes over oxygenator assembly 122, and exits via outlet port 115b. Diaphragm assemblies 114 and 119 form an active element that vibrates or agitates the blood to enhance diffusion of oxygen into, and carbon dioxide from, blood contained in compartment 111. Specifically, acoustic transducer 118 outputs a pulsed acoustic signal that causes diaphragms 116 and 120 to vibrate, thereby causing the column of blood contained within compartment 111 to shift upwards and downwards, as illustrated by the arrows in FIG. 7B. This movement is expected to induce turbulent mixing within compartment 111, and to disrupt the establishment of laminar flow zones and stagnation zones within the compartment. Oxygenated blood exits from compartment 111 via outlet port 115b and passes to valve 40, then through arterial filter 36 and outlet port 34 to return line 27, as described hereinabove.

Figure 8A:
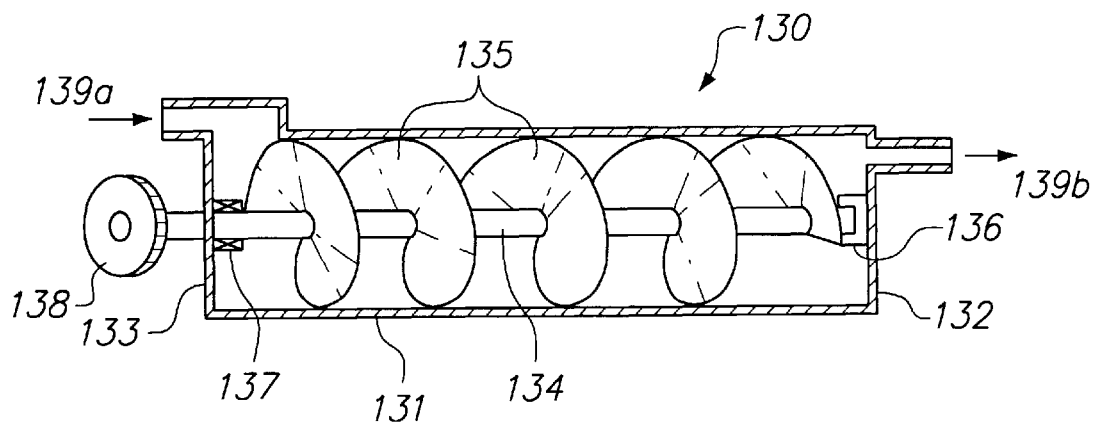
FIGS. 8A–8C are cross-sectional views of illustrative pump mechanisms suitable for use in the integrated system of the present invention.
Figure 8B:
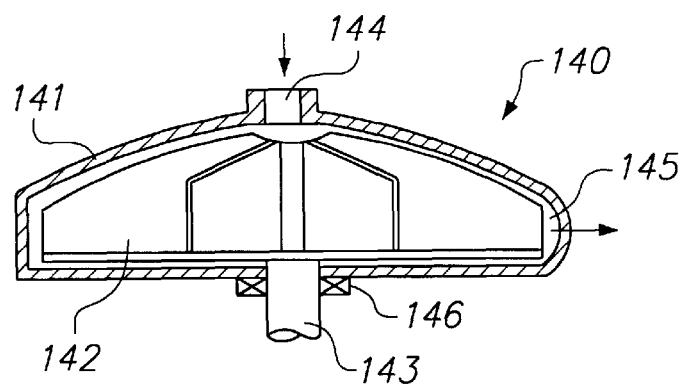
Figure 8C:
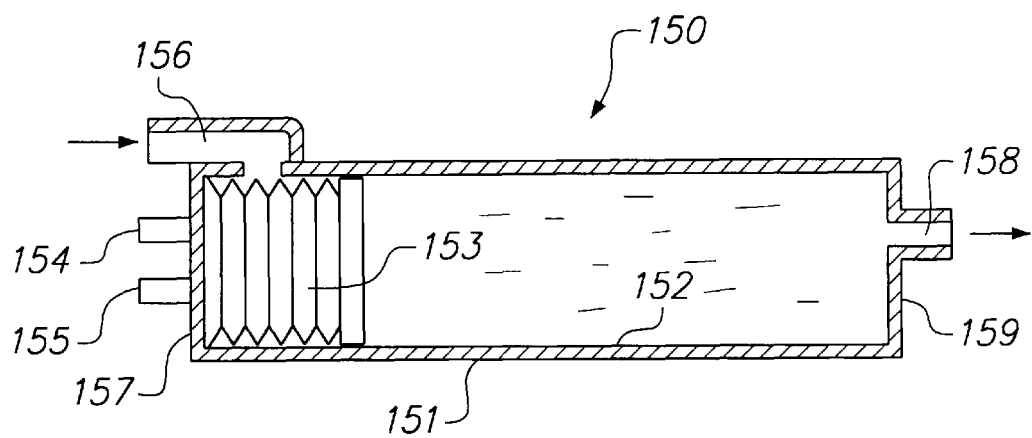

Referring now to FIGS. 8A to 8C, illustrative embodiments of pumps suitable for use in the integrated system of the present invention are described. Pumps suitable for use in the integrated system of the present invention preferably should provide maximum flow rates in the range of 7 to 8 liter/min. In FIG. 8A, pump 130 is an axial-type pump, and comprises cylinder 131 having endplates 132 and 133. Shaft 134 has spiral vane 135 extending along its length. Shaft 134 is engaged with thrust bearing 136 affixed to endplate 132, and extends through endplate 133 through fluid-tight bearing 137. Gearing arrangement 138, which may comprise suitably dimensioned spline gears, couple shaft 134 to gear train 48 (see FIGS. 3). Pump 130 has inlet port 139a disposed near endplate 133 and outlet port 139b disposed in endplate 132.

Spiral vane 135 extends from shaft 134 so that its outermost edge is disposed close to the interior surface of cylinder 131. In addition, vane 135 may include an elastomeric edge that sweeps along the interior of cylinder 131 as shaft 134 is rotated by gearing 138. Pump 130 therefore is a positive-displacement type pump, with each revolution of shaft 134 causing vane 135 to urge a predetermined volume of blood along a portion of cylinder 131 between inlet port 139a and outlet port 139b. Accordingly, the flow rate of pump 130 is proportional to the speed at which shaft 134 is rotated.

With respect to FIG. 8B, centrifugal pump 140 suitable for use in integrated blood oxygenator and pump unit 21 of the present invention is described. Pump 140 includes chamber 141, for example, molded from a high strength plastic, in which impeller 142 is disposed on shaft 143. Impeller 142 comprises a plurality of curved vanes that urge blood introduced into the center of the pump through inlet port 144 to flow outward, and exit the pump through outlet port 145. Shaft 143 passes through a fluid-tight bearing 146 and includes gearing (not shown) that couples the shaft to gear train 48 and shaft 43a of unit 21.

In FIG. 7C, another positive-displacement pump suitable for use in the present invention is described. Pump 150 comprises cylinder 151 forming chamber 152. Bellow-type piston 153 is disposed chamber 152 and is coupled to source of high pressure through port 154 and a vacuum source through port 155. Cylinder 151 includes inlet port 156 disposed at end 157 and outlet port 158 disposed in end 159. In operation, blood accumulates in cylinder 151 with bellows 153 in its contracted state, which is caused by selectively coupling bellows to the vacuum port through port 155. Once chamber 152 is filled, bellows 153 is uncoupled from the vacuum source, and high pressure gas is injected into the bellows through port 154. This in turn causes the bellows to expand, urging blood through outlet port 158. Alternatively, a piston driven by a rack-and pinion type gearing arrangement could be substituted for bellows-type piston 153.

As will of course be understood by one of skill in the art of pump designs, the foregoing pump embodiments are intended to be illustrative only, and other types of pump mechanisms may be readily employed in the present invention. For example, bladder-type and roller-type pumps also may be advantageously employed with the present invention. In addition, magnetic coupling may be employed for driving the shafts and impellers of the embodiments of FIGS. 8A and 8B, as described, for example, in U.S. Pat. No. 4,944,748 to Bramm et al. and U.S. Pat. No. 5,399,074 to Nose et al., which are incorporated herein by reference.

Figure 9A:
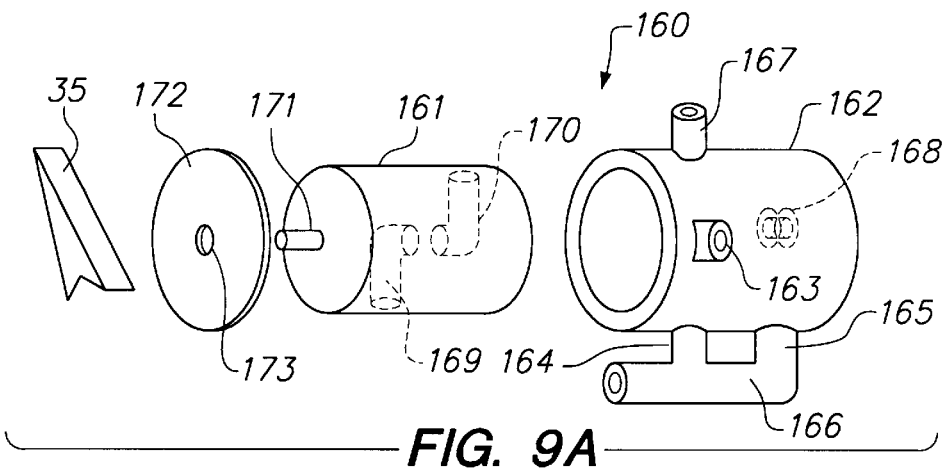
Figure 9B:
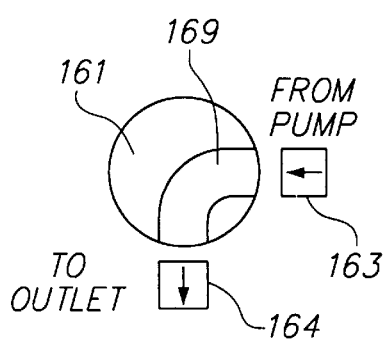
FIGS. 9B and 9C illustrate the flow paths established when the valve of FIG. 9A is in the pump-only and pump and oxygenator positions, respectively.
Figure 9C:
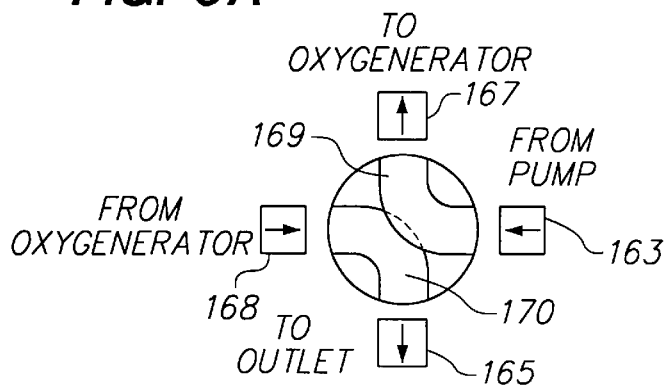

Referring now to FIGS. 9A through 9C, a valve suitable for use in the present invention is described. Valve 160 comprises valve body 161 disposed in housing 162. Body 161 comprises a high strength plastic, such as polycarbonate, having a plurality of channels molded or machined therein to define flow paths. Housing, which also may be formed of polycarbonate, includes inlet 163 from pump 37, outlets 164 and 165 coupled to outlet line 166, outlet 167 to blood oxygenator 38, and inlet 168 from blood oxygenator 38. Outlet line 166 is coupled to arterial filter 36 and outlet port 34.

Valve body 161 includes passageways 169 and 170 and shaft 171. When valve body 161 is disposed within housing 162, the exterior of body 161 establishes a smooth sliding contact with the interior of housing 162. Cover plate 172 is fastened to housing 162 by a suitable adhesive, and includes aperture 173 through which shaft 171 projects. When valve 160 is affixed within housing 30 of integrated blood oxygenator and pump unit 21, shaft 171 projects through the front surface of housing 30 to accept selector knob 35.

With respect to FIG. 9B, when selector knob 35 is positioned to select pump-only operation of unit 21, valve body 161 is oriented in housing 162 so that blood entering through inlet 163 passes directly through passageway 169 and outlet 164 into outlet line 166. In addition, this orientation of valve body 161 effectively blocks outlet 165 from communicating with outlet line 166, thereby preventing reverse flow into the oxygenator portion of the unit.

With respect to FIG. 9C, when selector knob 35 is rotated to the oxygenator position, e.g., about 90 degrees, passageway 169 is re-oriented so that one end is aligned with inlet 163 and the other end of the passageway is aligned with outlet 167 to the blood oxygenator. In addition, passageway 170 is moved so that one end is in alignment with inlet 168 from the blood oxygenator and the other end of the passageway is aligned with outlet 165 to outlet line 166. In this position, valve body 161 effectively blocks outlet 164 from communicating with outlet line 166.

Accordingly, when selector knob is moved to the oxygenator position, blood entering the valve through inlet 163 is directed to the blood oxygenator 38 through passageway 167, and oxygenated blood exiting the oxygenator via inlet 168 is directed to outlet line 166 via passageway 170. If, on the other hand, it is desired to employ system 20 in a pediatric cardiac application without using pump 37, outlet line 26 and return line 27 may be directly coupled to inlet and outlet ports 29a and 29b of unit 21, to provide blood oxygenation and low flow rate. In this latter case, selector knob 35 is left in the pump-only position, thereby isolating inlet port 167 and outlet port 168 from valve 160.

In view of the foregoing, it will be understood that integrated blood oxygenator and pump unit 21 may be advantageously used to reduce the pumping load of a beating heart during a first portion of a minimally invasive procedure, in which the pump is operated in pump-only mode, followed by placing the patient on full cardiopulmonary bypass for a portion of the surgical procedure requiring that the heart be stopped. The system therefore reduces the total time a patient is put on cardiopulmonary bypass, and thus reduces the potential for myocardial infarction. In addition, unit 21 may be advantageously used to provide back-up or emergency cardiopulmonary bypass capability during beating-heart cardiac procedures, and when complications arise during high-risk atherectomy or angioplasty. The system may alternatively be used in oxygenator-only mode where a low flow rate is desirable. The system of the present invention therefore provides a degree of flexibility heretofore unavailable.

Figure 10:
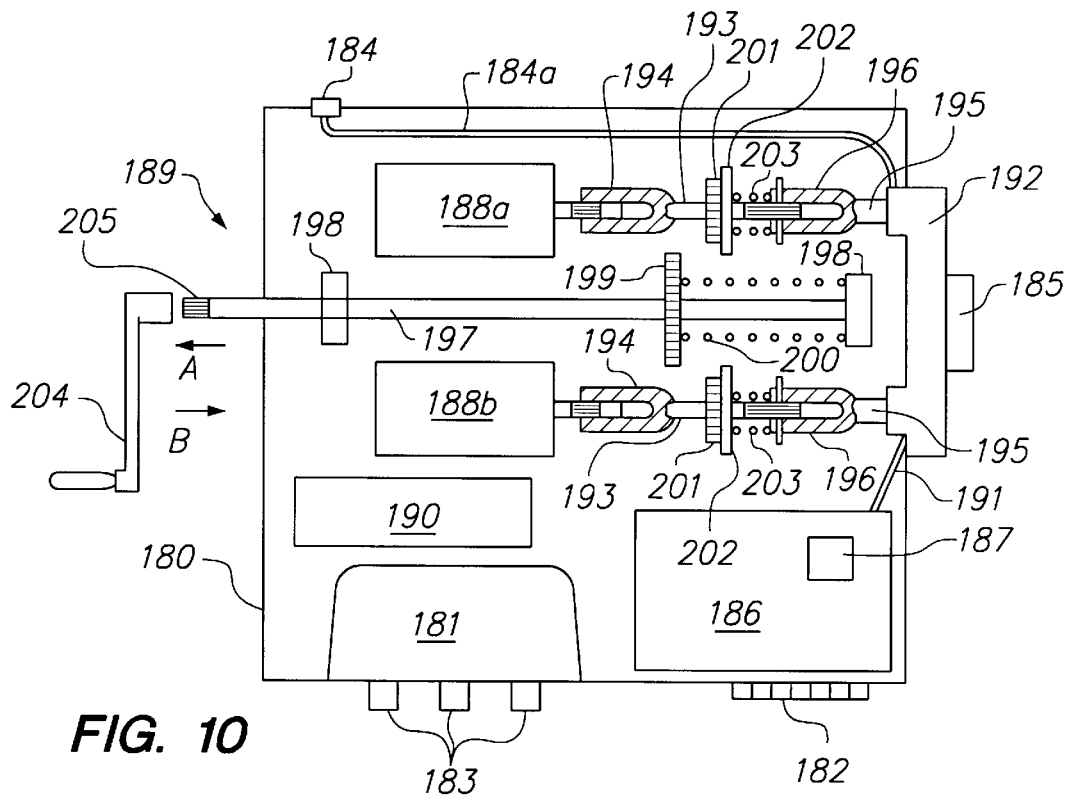
FIG. 10 is a plan view of a control console constructed in accordance with the principles of the present invention.

With respect to FIG. 10, control console 23 constructed in accordance with the present invention (see FIG. 1) is described. Control console 23 includes housing 180 having video screen 181, control panel 182, adjustment knobs 183, connector 184 for coupling to an oxygen tank, and connector 185 that accepts cable 25. Control console 180 houses electronics board 186 including microprocessor 187, variable speed motors 188a and 188b, emergency crank mechanism 189 and back-up battery 190. Housing 180 also includes piping 184a coupling connector 184 to a lumen of cable 25, and wiring 191 coupling electronics board 186 to oxygen saturation, oxygen pressure, carbon dioxide concentration, pressure, flow rate and pH sensors disposed in unit 21 (see FIG. 1).

Microprocessor 187 is programmed to control operation of variable speed motors 188a and 188b responsive to flow rate values input using control panel 182, to monitor blood gas parameter sensors, such as oxygen saturation, carbon dioxide, temperature, flow, and pressure sensors located in integrated blood oxygenation and pump unit 21, and to display graphs of the measured values on video screen 181. The blood gas parameter sensors, monitoring electronics, and display algorithms employed in control console 23 are per se known.

Microprocessor 187, which may be a 486 or Pentium®-class chip, may also be programmed to display, for example, blood pH and oxygen and carbon dioxide partial pressures, and blood temperature. Electronics board 186 may also include magnetic disk storage (not shown) to enable microprocessor 187 to periodically store samples of the desired values in a file for later review. Back-up battery 190 provides continued operation of electronics board 186 and microprocessor 187 in the event of a power outage.

Motors 188a and 188b are mounted within control console housing 180 and are coupled to drive cables 46a and 46b in cable 25 through transmission 192. Drive cables 46a and 46b are disposed in lumens of cable 25 (see FIG. 2) and transmit rotational motion imparted by motors 188a and 188b, respectively, to shafts 43a and 43b of unit 21, thereby driving the active element of the blood oxygenator 38 and pump 37.

Each of motors 188a and 188b is coupled to transmission 192 via shaft 193. The proximal end of shaft 193 includes motor spline assembly 194 that releasably engages the output shaft of the motor, while the distal end of shaft 193 slidably engages drive shaft 195 coupled to transmission 192 using output spline assembly 196. Emergency manual crank mechanism 189 includes shaft 197 mounted for reciprocation in bearings 198. Gear 199 is fixed to shaft 197, while spring 200 biases shaft 197 in direction A. Gears 201 and thrustplates 202 are mounted on each of shafts 193, and biased in direction A by spring 203. Hand crank 204 is mounted on end 205 of shaft 197 to periodically actuate pump 37 and blood oxygenator 38 in the event of a power outage.

Emergency crank mechanism 189 operates as follows: hand crank 204 is first placed on end 205 of shaft 197, and shaft 197 is pushed inward against the bias of spring 200. The resulting motion of shaft 197 causes gear 199 to engage gear 201 and thrustplate 202 on each of shafts 193. This motion in turn causes shafts 193 to move in direction B against the bias of springs 203, and also disconnects motor spline assemblies 194 from the output shafts of motors 188a and 188b. Hand crank 204 may then be turned, with the resulting rotational motion being transmitted from hand crank 204 to drive cables 46a and 46b through gears 199 and 201 and shafts 195 and transmission 192. When pressure on hand crank 204 in direction B is removed, springs 200 and 203 again urge shafts 197 and 193 in direction A, thus causing motor spline assemblies 194 to again couple the output shafts of motors 188a and 188b to shafts 193.

While preferred illustrative embodiments of the invention are described above, it will be apparent to one skilled in the art that various changes and modifications may be made therein without departing from the invention and it is intended in the appended claims to cover all such changes and modifications which fall within the true spirit and scope of the invention.

What is claimed is:

1. A system for processing blood during a surgical procedure comprising:
   an extracorporeal housing having a system inlet and a system outlet;
   a blood pump disposed within the extracorporeal housing and comprising a plurality of vanes affixed to a first shaft;
   a first variable-speed motor coupled to the first shaft to drive the first shaft at a first rotational speed;
   an oxygenator disposed within the extracorporeal housing and coupled to the blood pump, the oxygenator comprising a multiplicity of hollow fibers affixed to a second shaft, the second shaft having a gas inlet lumen and a gas outlet lumen, each one of the multiplicity of fibers having a first end coupled to a gas inlet manifold communicating with the gas inlet lumen and a second end coupled to a gas outlet manifold communicating with the gas outlet lumen, rotation of the second shaft generating a pressure head; and
   a second variable-speed motor coupled to the second shaft to drive the second shaft at a second rotational speed; and
   a controller coupled to the first and second variable-speed motors, the controller programmed to vary the second rotational speed responsive to changes in the first rotational speed to provide a user-selected blood flow rate at the system outlet.

2. The system of claim 1 further comprising a blood reservoir coupled to the system inlet.

3. The system of claim 1 further comprising a heat exchanger coupled to the system outlet.

4. The system of claim 1 further comprising a valve having a first position wherein the blood pump is coupled to the oxygenator and a second position wherein the blood pump is isolated from the oxygenator.

5. The system of claim 1 wherein the oxygenator further comprises:
   a ring having portions defining the gas inlet manifold and the gas outlet manifold;
   a first plurality of hollow spokes coupling the gas inlet lumen in fluid communication with the gas inlet manifold; and
   a second plurality of hollow spokes coupling the gas outlet lumen in fluid communication with the gas outlet manifold.

6. The system of claim 1 wherein the blood pump and oxygenator are housed within a unit configured to be placed in a sterile field adjacent to an operating table.

7. The system of claim 6 further comprising:
   a control console housing the controller and the first and second variable-speed motors.

8. The system of claim 7 wherein the control console further comprises an emergency crank mechanism that enables the blood pump to be actuated in case of power outage.

9. Apparatus for extracorporeally processing blood during a surgical procedure comprising:
   a housing having a system inlet and a system outlet;
   a blood pump disposed within the housing and comprising a plurality of vanes affixed to a first shaft;
   a first variable-speed motor coupled to the first shaft to drive the first shaft at a first rotational speed;
   an oxygenator disposed within the housing and coupled to the blood pump, the oxygenator comprising a multiplicity of hollow fibers affixed to a second shaft, each one of the multiplicity of hollow fibers having a first end potted in a gas inlet manifold and a second end potted in a gas outlet manifold;
   a second variable-speed motor coupled to the second shaft to drive the second shaft at a second rotational speed; and
   a controller coupled to the first and second variable-speed motors, the controller programmed to vary the second rotational speed responsive to changes in t he first rotational speed to provide a user-selected blood flow rate and oxygenation level at the system outlet.

10. The apparatus of claim 9 further comprising a blood reservoir coupled to the system inlet.

11. The apparatus of claim 9 wherein the oxygenator further comprises:
   a shaft having first and second lumens;
   a ring having portions defining the gas inlet manifold and the gas outlet manifold;
   a first plurality of hollow spokes coupling the first lumen in fluid communication to the gas inlet manifold; and
   a second plurality of hollow spokes coupling the second lumen in fluid communication to the gas outlet manifold.

12. The apparatus of claim 9 wherein the blood pump and oxygenator are housed within a unit configured to be placed in a sterile field adjacent to an operating table.

13. The apparatus of claim 12 further comprising:
   a control console housing the controller and the first and second variable-speed motors.

14. The apparatus of claim 13 wherein the control console further comprises an emergency crank mechanism that enables the blood pump to be actuated in case of power outage.

15. A method of extracorporeally processing blood during a surgical procedure comprising:

provviding apparatus comprising a controller and a housing having an inlet and an outlet, the housing enclosing a blood pump comprising a plurality of vanes affixed to a first shaft and an oxygenator having a second shaft and a multiplicity of hollow fibers affixed to the second shaft, each one of the multiplicity of hollow fibers having a first end coupled to a gas inlet manifold and a second end coupled to a gas outlet manifold;

inputting to the controller a user-selected blood flow rate and oxygenation level at the outlet;

receiving blood through the inlet;

rotating the first shaft at a first speed to circulate blood under pressure to the oxygenator; and rotating the second shaft at a second speed to oxygenate the blood supplied to the oxygenator and to circulate oxygenated blood under pressure to the outlet; and adjusting the first and second speeds to supply oxygenated blood to the outlet at the user-selected blood flow rate and oxygenation level.

* * * * *